(12) United States Patent
Uchino

(10) Patent No.: US 11,413,229 B2
(45) Date of Patent: Aug. 16, 2022

(54) ORAL PLAQUE DISPERSION AGENT

(71) Applicant: KAO CORPORATION, Tokyo (JP)

(72) Inventor: Yosuke Uchino, Mitaka (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 16/329,963

(22) PCT Filed: Aug. 31, 2017

(86) PCT No.: PCT/JP2017/031460
§ 371 (c)(1),
(2) Date: Mar. 1, 2019

(87) PCT Pub. No.: WO2018/043677
PCT Pub. Date: Mar. 8, 2018

(65) Prior Publication Data
US 2019/0201302 A1 Jul. 4, 2019

(30) Foreign Application Priority Data
Sep. 2, 2016 (JP) .............................. JP2016-172116

(51) Int. Cl.
*A61K 8/34* (2006.01)
*A61K 8/41* (2006.01)
*A61Q 11/00* (2006.01)
*A61K 8/42* (2006.01)
*A61K 8/43* (2006.01)

(52) U.S. Cl.
CPC ............... *A61K 8/345* (2013.01); *A61K 8/34* (2013.01); *A61K 8/41* (2013.01); *A61K 8/416* (2013.01); *A61K 8/42* (2013.01); *A61K 8/43* (2013.01); *A61Q 11/00* (2013.01)

(58) Field of Classification Search
CPC .......... A61Q 11/00; A61K 8/34; A61K 8/345; A61K 8/43; A61K 8/41; A61K 8/416; A61K 8/42; A61P 1/02
See application file for complete search history.

(56) References Cited

U.S. PATENT DOCUMENTS

| 4,726,943 A | 2/1988 | Klueppel et al. | |
|---|---|---|---|
| 5,900,230 A | 5/1999 | Cutler et al. | |
| 7,510,859 B2* | 3/2009 | Wieland ............. | C11D 3/38636 424/401 |
| 8,460,689 B2* | 6/2013 | Wlaschin ............. | A61M 16/04 424/405 |
| 2010/0285148 A1 | 11/2010 | Wlaschin et al. | |
| 2013/0298911 A1 | 11/2013 | Wlaschin et al. | |
| 2013/0303483 A1 | 11/2013 | Yamamoto | |
| 2016/0022568 A1 | 1/2016 | Patel | |

FOREIGN PATENT DOCUMENTS

| CN | 105307633 | | 2/2016 |
|---|---|---|---|
| JP | 58-39620 | A | 3/1958 |
| JP | 5-229923 | A | 9/1993 |
| JP | 6-256167 | A | 9/1994 |
| JP | 8-217653 | A | 8/1996 |
| JP | 11-100315 | A | 4/1999 |
| JP | 2000-281547 | A | 10/2000 |
| JP | 2005-29484 | A | 2/2005 |
| JP | 2007-210913 | A | 8/2007 |
| JP | 2009-114125 | A | 5/2009 |
| JP | 2010-235457 | A | 10/2010 |
| JP | 2012-526142 | | 10/2012 |
| JP | 2013-124220 | A | 6/2013 |
| JP | 2015-20970 | A | 2/2015 |
| JP | 2015-028123 | | 2/2015 |
| JP | 2015-164904 | | 9/2015 |
| JP | 2019-116449 | A | 7/2019 |
| WO | WO2010/129795 | | 11/2010 |
| WO | WO 2012/093643 | A1 | 7/2012 |
| WO | WO 2015/157241 | A1 | 10/2015 |

OTHER PUBLICATIONS

ICIS (Chemical profile: pentaerythritol) pp. 1-2 (Year: 2007).*
EWG Skin Deep® | What is Triethanolamine pp. 1-8 (Year: 2020).*
International Search Report dated Oct. 3, 2017 in PCT/JP2017/031460 filed Aug. 31, 2017.
Yano, Y. et al. "Availability of erythritol on oral health care," Fragrance Journal, vol. 36, No. 6, Jun. 15, 2008, pp. 13-18 (with English abstract).
Extended European Search Report dated Mar. 30, 2020 in European Patent Application No. 17846681.9, 9 pages.
Database GNPD[Online] MINTEL; May 19, 2016, Anonymous: "Bubble Gum Flavored Dental Cleaning Gel for Kids with Fluoride", XP55676609, retrieved from www.gnpd.com, Database Accession No. 4005699, 4 pages.
Database GNPD[Online] MINTEL; Jun. 29, 2016, Anonymous: "Mouthwash", XP55676610, retrieved from www.gnpd.com, Database Accession No. 4090209, 4 pages.

* cited by examiner

*Primary Examiner* — Lezah Roberts
(74) *Attorney, Agent, or Firm* — Oblon, McClelland, Maier & Neustadt, L.L.P.

(57) ABSTRACT

The present invention relates to an oral plaque dispersion agent capable of effectively acting on dental plaque from the surface layer to the deep part thereof and exerting an excellent effect of dispersing the dental plaque. Specifically, the present invention relates to an oral plaque dispersion agent comprising (A) a water-soluble compound 3 or more of primary hydroxyl groups in the molecular structure and 100 or more and 200 or less of a chemical formula weight as an active component.

15 Claims, No Drawings

ORAL PLAQUE DISPERSION AGENT

FIELD OF THE INVENTION

The present invention relates to an oral plaque dispersion agent.

BACKGROUND OF THE INVENTION

Conventionally, sugar alcohols and polyhydric alcohols which have hydroxyl groups in the molecular structures, such as erythritol, pentaerythritol, polyethylene glycol and glycerin, are used for various agents and compositions for intraoral applications. Specifically, these components are capable of producing a good flavor as flavoring components as described in Patent Literature 1, or contributing to inhibition of dry mouth as a wetting agent or a moisturizer as described in Patent Literatures 2 and 3, for example.

Meanwhile, among these sugar alcohols, for example, xylitol is known as a component capable of suppressing that dental plaque (plaque), which is a type of biofilm, is formed by various bacteria existing in the mouth. Patent Literatures 4 and 5 disclose an oral composition containing such xylitol and dextranase or xylitol and sulfated glucan or a water-soluble salt thereof.

Patent Literature 1: JP-A-2009-114125
Patent Literature 2: JP-A-2013-124220
Patent Literature 3: JP-A-2010-235457
Patent Literature 4: JP-A-11-100315
Patent Literature 5: JP-A-2000-281547

SUMMARY OF THE INVENTION

The present invention relates to an oral plaque dispersion agent comprising (A) a water-soluble compound having 3 or more of primary hydroxyl groups in the molecular structure and 100 or more and 200 or less of a chemical formula weight as an active component.

Such dental plaque is, more specifically, an aggregate mass which is formed of exopolysaccharides (EPS) produced by intraoral bacteria, is firmly deposited on tooth surface, and has bacteria growing inside and in the deep part of the dental plaque. EPS mainly contains insoluble glucan existing therein, and as dental plaque increases, the proportion of insoluble glucan existing in the EPS surface layer increases. EPS then accelerates the bacterial growth while functioning as a barrier for protecting bacteria inside the dental plaque from the outside world.

However, the technology using xylitol described in Patent Literatures 4 and 5 above can prevent formation of dental plaque, but is unable to sufficiently act on even the deep part of the dental plaque while disrupting the EPS surface layer. Thus the technology still needs further improvement for effectively dispersing and removing the firmly formed dental plaque.

Therefore, the present invention provides an oral plaque dispersion agent capable of effectively acting on dental plaque from the surface layer to the deep part thereof and exerting an excellent effect of dispersing the dental plaque.

As a result of intensive studies, the present inventor discovered that an oral plaque dispersion agent capable of exerting an excellent effect of removing dental plaque can be obtained by containing a water-soluble compound having specific amount of specific hydroxyl groups in the molecular structure and a specific chemical formula weight as an active component.

The oral plaque dispersion agent of the present invention is capable of effectively dispersing and removing not only the surface layer but also the deep part of firmly formed dental plaque, and thus is capable of preventing mouth diseases such as caries, periodontal disease, and halitosis.

DETAILED DESCRIPTION OF THE INVENTION

Hereinafter, the present invention will be described specifically.

The oral plaque dispersion agent of the present invention contains, as an active component, component (A) which is a water-soluble compound having 3 or more of primary hydroxyl groups in the molecular structure and 100 or more and 200 or less of a chemical formula weight. Insoluble glucan mainly existing in EPS is a polymer in which D-glucoses are linked via glycosidic linkages each other. The present inventor has focused on the fact that many intramolecular hydrogen bondings are present at various spots in the polymer structure, considered that 3 or more primary hydroxyl groups existing in the molecular structure of component (A) is effective for blocking the hydrogen bonding in the polymer so as to weaken the firm aggregation property of dental plaque, and thus discovered that component (A) is useful as an active component for effectively dispersing dental plaque.

The number of primary hydroxyl groups in the molecular structure of component (A) is 3 or more, preferably 4 or more in view of effectively weakening dental plaque due to blocking of hydrogen bonding to exert a high effect of dispersing dental plaque, and is preferably 6 or less, more preferably 5 or less in view of availability; and the number is preferably 4.

Component (A) is a water-soluble compound, and such component (A) has a solubility to 100 g of water at 20° C. of preferably 3 g/100 g or more, more preferably from 5 to 70 g/100 g, still more preferably from 5 to 60 g/100 g.

In view of possession of the above effective number of primary hydroxyl groups in the molecular structure of component (A), in view of effective blocking of hydrogen bonding to exert a high effect of dispersing dental plaque, and in view of availability, component (A) has a chemical formula weight of 100 or more, preferably 120 or more, more preferably 130 or more, and 200 or less, preferably 180 or less, more preferably 160 or less.

Note that the chemical formula weight of component (A) is namely the molecular weight of component (A), and is determined from the total sum of the atomic weights of component elements when component (A) is represented by a chemical formula.

Examples of component (A) include, more specifically, preferably one or more selected from the group consisting of pentaerythritol, trimethylolmethane, trimethylolethane, trimethylolpropane, tris(hydroxymethyl)aminomethane, and triethanolamine. Among them, in view of the above effective number of primary hydroxyl groups in the molecular structure, in view of effective blocking of hydrogen bonding to exert a high effect of dispersing dental plaque, and in view of availability, examples of component (A) include more preferably one or more selected from the group consisting of pentaerythritol, trimethylolethane, trimethylolpropane, tris (hydroxymethyl)aminomethane, and triethanolamine. In view of further ensuring a good feeling upon use, examples of component (A) include still more preferably one or more selected from the group consisting of pentaerythritol, trimethylolethane, and trimethylolpropane; still more preferably pentaerythritol.

Further specifically, for example, pentaerythritol has an English name "pentaerythritol", a chemical formula weight of 136.15, and solubility to water at 15° C. of 5.6 g/100 mL, and is commercially available from Nippon Synthetic Chemical Industry Co., Ltd., Tokyo Chemical Industry Co., Ltd., and Toyo Chemicals Co., Ltd., for example.

Trimethylolethane is also referred to as 1,1,1-tris(hydroxymethyl)ethane, having a chemical formula weight of 120.15, and solubility to water at 20° C. of 60 g/100 mL.

Tris(hydroxymethyl)aminomethane has an English name "Tris(hydroxymethyl)aminomethane", a chemical formula weight of 121.14, and solubility to water at 25° C. of 50 g/100 mL.

Triethanolamine has an English name "Triethanolamine" and is also referred to as tris(2-hydroxyethyl)amine, having a chemical formula weight of 149.19 and being readily soluble to water.

Trimethylolpropane has an English name "Trimethylolpropane" and is also referred to as 1,1,1-tris(hydroxymethyl) propane, having a chemical formula weight of 134.18 and being readily soluble to water.

In view of blocking hydrogen bonding and thus effectively weakening dental plaque to exert a high effect of dispersing dental plaque, the content of component (A) in the oral plaque dispersion agent of the present invention is preferably 0.2% by mass or more, more preferably 1% by mass or more, still more preferably 2% by mass or more, further more preferably 4% by mass or more. Moreover, in view of ensuring the intraoral solubility or dispersibility of component (A), the content of component (A) is preferably 20% by mass or less, more preferably 18% by mass or less, still more preferably 15% by mass or less. Furthermore, the content of component (A) in the oral plaque dispersion agent of the present invention ranges preferably from 0.2 to 20% by mass, more preferably from 1 to 20% by mass, still more preferably from 2 to 18% by mass, still more preferably from 4 to 15% by mass.

The oral plaque dispersion agent of the present invention still more preferably contains, as component (B), a sugar alcohol (B) having 2 of primary hydroxyl groups in the molecular structure. Such component (B) alone can exert a limited effect of dispersing dental plaque, however, combined use of component (B) with the above component (A) can further enhance the effect of dispersing dental plaque and thus can effectively remove the dental plaque.

Examples of component (B) include preferably one or more components (B1) selected from the group consisting of erythritol, xylitol, reduced palatinose, and mannitol in view of ensuring an excellent effect of dispersing dental plaque, and thus effectively removing the dental plaque; and preferably one or two components (B2) selected from the group consisting of sorbitol and glycerin in view of solubility and wettability, and flavor. Among them, in view of ensuring an excellent effect of dispersing dental plaque, and thus effectively removing the dental plaque, the oral plaque dispersion agent of the present invention preferably contains component (B1) as component (B), more preferably contains one or two selected from the group consisting of erythritol and xylitol, still more preferably contains erythritol.

In view of ensuring an excellent effect of dispersing dental plaque, and imparting a good flavor, the content of component (B1) is in the oral plaque dispersion agent of the present invention is preferably 1% by mass or more, more preferably 2% by mass or more, still more preferably 3% by mass or more, further preferably 5%, by mass or more. Moreover, in view of further enhancing the effect of removing dental plaque, and thus effectively removing the dental plaque, the content of component (B1) is in the oral plaque dispersion agent of the present invention is preferably 55% by mass or less, more preferably 50% by mass or less, still more preferably 40% by mass or less, further preferably 30% by mass or less. Then, the content of component (B1) in the oral plaque dispersion agent of the present invention ranges from preferably from 1 to 55% by mass, more preferably from 2 to 50% by mass, still more preferably from 3 to 40% by mass, still more preferably from 5 to 30% by mass.

More specifically, for example, when the oral plaque dispersion agent of the present invention is a dentifrice such as a toothpaste or a tooth powder, the content of component (B1) in the oral plaque dispersion agent of the present invention is preferably 5% by mass or more, more preferably 10% by mass or more, still more preferably 15% by mass or more, and preferably 55% by mass or less, more preferably 50% by mass or less, still more preferably 45% by mass or less.

Moreover, when the oral plaque dispersion agent of the present invention is a liquid such as a mouthwash or a liquid dentifrice, the content of component (B1) in oral plaque dispersion agent of the present invention is preferably 1% by mass or more, more preferably 2% by mass or more, still more preferably 3% by mass or more, and preferably 20% by mass or less, more preferably 15% by mass or less, still more preferably 12% by mass or less.

In view of ensuring good flavor and a wetting effect, the content of component (B2) in the oral plaque dispersion agent of the present invention ranges preferably from 1 to 30% by mass, more preferably from 2 to 25% by mass, still more preferably from 3 to 20% by mass.

More specifically, for example, when the oral plaque dispersion agent of the present invention is a dentifrice such as a toothpaste or a tooth powder or a liquid for a foam discharging container, the content of component (B2) in the oral plaque dispersion agent of the present invention ranges preferably from 3 to 30% by mass, more preferably from 5 to 25% by mass, still more preferably from 10 to 20% by mass. Furthermore, when the oral plaque dispersion agent of the present invention is a liquid such as a mouthwash or a liquid dentifrice, the content of component (B2) in the oral plaque dispersion agent of the present invention ranges preferably from 1 to 20% by mass, more preferably from 2 to 15% by mass, still more preferably from 3 to 12% by mass.

In view of ensuring an excellent effect of dispersing dental plaque, the mass ratio of component (A) to component (B1), (A)/(B1), is preferably 0.01 or more, more preferably 0.05 or more, still more preferably 0.1 or more, further preferably 0.2 or more. In view of effectively removing dental plaque with a high effect of dispersing the dental plaque, the mass ratio of component (A) to component (B1), (A)/(B1), is preferably 10 or less, more preferably 5 or less, still more preferably 3 or less, still more preferably 1 or less, still more preferably 0.8 or less. Moreover, the mass ratio of component (A) to component (B1), (A)/(B1), ranges preferably from 0.01 to 10, more preferably from 0.01 to 5, still more preferably from 0.05 to 3, still more preferably from 0.1 to 1, still more preferably from 0.2 to 0.8.

More specifically, for example, when the oral plaque dispersion agent of the present invention is a toothpaste or a jel dentifrice, in view of ensuring an excellent effect of dispersing dental plaque, the mass ratio of component (A) to component (B1), (A)/(B1), is preferably 0.01 or more, more preferably 0.05 or more, still more preferably 0.1 or more, further preferably 0.2 or more; and in view of effectively removing dental plaque with a high effect of dispersing the dental plaque, preferably 3 or less, more preferably 2 or less, still more preferably 1 or less, still more preferably 0.8 or less.

Moreover, when the oral plaque dispersion agent of the present invention is a liquid such as a mouthwash or a liquid dentifrice, in view of ensuring an excellent effect of dispersing dental plaque, the mass ratio of component (A) to component (B1), (A)/(B1), is preferably 0.01 or more, more preferably 0.1 or more, still more preferably 0.2 or more, still more preferably 0.4 or more; and in view of effectively removing dental plaque with a high effect of dispersing the dental plaque, preferably 10 or less, more preferably 5 or less, still more preferably 3 or less.

The oral plaque dispersion agent of the present invention further preferably contains, as component (C), one or more protein-denaturing agents selected from the group consisting of urea, guanidine or a salt thereof, and an anionic surfactant. Although such component (C) is a component exerting an effect of denaturing proteins, it is difficult for component (C) alone to sufficiently enhance the effect of dispersing dental plaque, but a combination of component (C) with component (A) makes it possible to effectively enhance the effect of dispersing dental plaque.

Examples of a guanidine salt include acid addition salts such as a hydrochloride and a sulfate.

Examples of an anionic surfactant include a higher fatty acid salt, a bile salt and a derivative thereof, an alkyl sulfate ester salt, an alkylsulfonate salt, an alkyl phosphate ester salt, a polyoxyalkylene alkyl sulfate ester salt, a polyoxyalkylene alkylsulfonate salt, a polyoxyalkylene alkyl phosphate ester salt, an N-acyl amino acid salt, an alkylmethyl taurate salt, a sulfosuccinate ester salt, and alkylbenzenesulfonate salt. The number of carbon atoms of the alkyl moiety or the aliphatic acyl moiety of these anionic surfactants preferably ranges from 8 to 24. Particularly, examples of a more preferable anionic surfactant include an alkyl sulfate ester salt having 8 to 24 carbon atoms, an N-acyl sarcosine salt in which the acyl group has 8 to 24 carbon atoms; and an alkylmethyl taurate salt and an N-acyl acidic amino acid salt having 8 to 24 carbon atoms.

In view of synergistically enhancing the effect of dispersing dental plaque in the mouth through the use thereof in combination with component (A), the content of a protein-denaturing agent as component (C) in the oral plaque dispersion agent of the present invention is preferably 0.001% by mass or more, more preferably 0.005% by mass or more, still more preferably 0.01% by mass or more, still more preferably 0.1% by mass or more, and preferably 1% by mass or less, more preferably 0.8% by mass or less, still more preferably 0.5% by mass or less.

More specifically, for example, when the oral plaque dispersion agent of the present invention is a dentifrice such as a toothpaste or a tooth powder, in view of ensuring an excellent effect of dispersing dental plaque even while the dentifrice is diluted with saliva during tooth brushing and further in view of synergistically enhancing the effect of dispersing dental plaque through the use thereof in combination with component (A), the content of a protein-denaturing agent as component (C) in the oral plaque dispersion agent of the present invention is preferably 0.1% by mass or more, more preferably 0.2% by mass or more; and in view of inhibiting the protein-denaturing effect from damaging intraoral mucosa, preferably 2% by mass or less, more preferably 1.5% by mass or less, still more preferably 1.2% by mass or less.

In the oral plaque dispersion agent of the present invention, in view of causing dental plaque to contain water while blocking hydrogen bonding inside the dental plaque so as to effectively weaken the dental plaque, the water content in the oral plaque dispersion agent of the present invention is preferably 50% by mass or more, more preferably 55% by mass or more, still more preferably 60% by mass or more, and preferably 99% by mass or less, more preferably 95% by mass or less, still more preferably 90% by mass or less. Furthermore, when the oral plaque dispersion agent of the present invention comprises component (B), component (C), or component (B) and component (C), the water content in the oral plaque dispersion agent of the present invention is preferably 90% by mass or less, more preferably 85% by mass or less. Further, the water content in the oral plaque dispersion agent of the present invention ranges preferably from 50 to 99% by mass, more preferably from 55 to 95% by mass, still more preferably from 60 to 90% by mass. Furthermore, when the oral plaque dispersion agent of the present invention comprises component (B), component (C), or component (B) and component (C), the water content in the oral plaque dispersion agent of the present invention ranges preferably from 50 to 90% by mass, more preferably from 55 to 85% by mass, still more preferably from 60 to 85% by mass.

Moreover, when the oral plaque dispersion agent of the present invention is a dentifrice such as a toothpaste or a tooth powder, in view of ensuring intraoral dispersibility and melt-in-the-mouth feeling while maintaining appropriate viscosity, the water content in the oral plaque dispersion agent of the present invention is preferably 12% by mass or more, more preferably 15% by mass or more, and preferably 55% by mass or less, more preferably 50% by mass or less, still more preferably 45% by mass or less.

In view of that component (A) provides the high effect of dispersing dental plaque as an active component and thus can exert a sufficient effect even when its concentration is supposed to be low, and in view of cost, the mass ratio of component (A) to water, (A)/water, is preferably 0.01 or more, more preferably 0.02 or more, still more preferably 0.05 or more. Further, in view of ensuring a balance between solubility of component (A) to water and the effect of dispersing dental plaque, the mass ratio of component (A) to water, (A)/water, is preferably 0.5 or less, more preferably 0.3 or less, still more preferably 0.2 or less. Moreover, the mass ratio of component (A) to water, (A)/water, ranges preferably from 0.01 to 0.5, more preferably from 0.02 to 0.3, still more preferably from 0.05 to 0.2.

More specifically, for example, when the oral plaque dispersion agent of the present invention is a dentifrice such as a toothpaste or a tooth powder, in view of ensuring the effect of dispersing dental plaque provided by component (A) as an active component, the mass ratio of component (A) to water, (A)/water, is preferably 0.02 or more, more preferably 0.04 or more, still more preferably 0.08 or more, and further more preferably 0.1 or more; and in view of sustaining the effect of dispersing dental plaque even upon dilution with saliva during the use of the dentifrice, the mass ratio of component (A) to water, (A)/water, is preferably 2 or less, more preferably 1.5 or less, still more preferably 1 or less, further preferably 0.8 or less.

The oral plaque dispersion agent of the present invention may further contain a cationic bactericide. The oral plaque dispersion agent of the present invention enables to spread such a cationic bactericide to every deep parts and details, while effectively dispersing dental plaque, and thus can cause the bactericide to effectively adsorb to the oral tissue surfaces such as tooth surface that has been blocked from the outside world by the dental plaque, and to effectively exert its bactericidal effect. A cationic bactericide exerts a bactericidal effect against bacteria, which cause dental caries, periodontal disease, halitosis, and the like. Examples of such a cationic microbicide include a quaternary ammonium compound and a biguanide compound. Examples of a cationic bactericide belonging to the quaternary ammonium compound include cetylpyridinium chloride, benzethonium chloride, dequalium chloride, benzalkonium chloride, alkyl dimethyl ammonium chloride, alkyl trimethyl ammonium chloride, and methylbenzethonium chloride. Furthermore, examples of a cationic bactericide belonging to the biguanide compound can include chlorhexidine and a salt thereof, and are preferably chlorhexidine gluconate and chlorhexidine hydrochloride. As a cationic bactericide, one or more selected from the group consisting of these examples are preferably used. Such a cationic bactericide is more preferably a quaternary ammonium compound, and is more preferably one or two selected from the group consisting of cetylpyridinium chloride and benzethonium chloride.

In view of ensuring bactericidal performance, suppressing bitter taste, pharmaceutical limitation, and the like, the content of a cationic bactericide in the oral plaque dispersion agent of the present invention is preferably 0.01% by mass or more, more preferably 0.02% by mass or more, still more preferably 0.03% by mass or more, and preferably 0.1% by mass or less, more preferably 0.08% by mass or less, still more preferably 0.07% by mass or less. Moreover, the content of a cationic bactericide in the oral plaque dispersion agent of the present invention ranges preferably from 0.01 to 0.1% by mass, more preferably 0.02 to 0.08% by mass, still more preferably from 0.03 to 0.07% by mass.

The oral plaque dispersion agent of the present invention can comprise the following components, in addition to the above components, as long as the effects of the present invention are not inhibited:
one or more nonionic surfactants selected from the group consisting of polyoxyethylene hydrogenated castor oil; sucrose fatty acid ester; sorbitan fatty acid ester; glycerol fatty acid esters such as monoglycerol stearate, decaglycerol monostearate, and pentaglycerol monomyristate; alkylglycoside; polyoxyethylene alkyl ethers such as polyoxyethylene monoalkyl (or alkenyl) ether, and polyoxyethylene polyoxypropylene copolymer; polyoxyethylene alkyl phenyl ethers such as polyoxyethylenenonylphenyl ether; amine oxide-based surfactant; fatty acid alkanolamides such as mono- (or di-)ethanolamide, and coconut oil fatty acid diethanolamide; polyglyceryl fatty acid esters such as decaglyceryl laurate; and polyglycol such as polyethylene polypropylene glycol;
one or two or more amphoteric surfactants selected from the group consisting of acetic acid betaine such as lauryldimethylaminoacetic acid betaine, imidazolium betaine such as 2-alkyl-N-carboxymethyl-N-hydroxyethyl-N-imidazolium betaine, alkylsulfobetaine such as lauryl sulfobetaine and lauryl hydroxysulfobetaine, coconut oil fatty acid amidoalkyl betaine such as coconut oil fatty acid amidopropyl betaine, and long chain alkylimidazolinebetaine salts such as sodium alkyl-1-hydroxyethylimidazolinebetaine;
a wetting agent selected from the group consisting of propylene glycol, 1,3-butylene glycol, polyethylene glycol, and dipropylene glycol;
a binder such as sodium alginate, sodium carboxymethyl cellulose, carrageenan, xanthan gum, sodium polyacrylate, hydroxyethylcellulose, hydroxypropylcellulose, pectin, gum traganth, gum arabic, guar gum, karaya gum, locust bean gum, gellan gum, tamarind gum, psyllium seed gum, polyvinyl alcohol, sodium chondroitin sulfate, and methoxyethylene-maleic anhydride copolymer;
an abrasive such as abrasive silica (oil absorption ranges from 50 to 150 mL/100 g. Such oil absorption means a value measured by the method according to JIS K5101-13-2 (established in 2004));
thickening silica (oil absorption measured by the method according to JIS K5101-13-2 (established in 2004) ranges from 200 to 400 mL/100 g);
a foaming aid; a preservative such as isobutyl parahydroxybenzoate, isopropyl parahydroxybenzoate, and ethyl parahydroxybenzoate; a pigment; a coloring; flavor, and the like, as appropriate.

The form of the oral plaque dispersion agent of the present invention may be in a form of liquid such as a liquid agent (e.g., a mouthwash or a liquid dentifrice) or may be in a form of gel, paste or gel such as a dentifrice (e.g., a toothpaste or a tooth powder, or a gel dentifrice). Moreover, the agent may also be in a form of liquid agent such as a liquid for a foam discharging container, which is charged in the foam discharging container and then discharged as foam from the discharge port when used.

Regarding the above embodiments of the present invention, the following oral plaque dispersion agent is disclosed.

[1] An oral plaque dispersion agent comprising (A) a water-soluble compound (A) having 3 or more of primary hydroxyl groups in the molecular structure and 100 or more and 200 or less of a chemical formula weight as an active component.

[2] The oral plaque dispersion agent according to [1] above, wherein the number of primary hydroxyl groups in the molecular structure of the component (A) is preferably 4 or more, and preferably 6 or less, more preferably 5 or less in view of availability, and the number is preferably 4.

[3] The oral plaque dispersion agent according to [1] or [2] above, wherein a solubility of the component (A) to 100 g of water at 20° C. is preferably 5 g/100 g or more, more preferably ranges from 10 to 60 g/100 g.

[4] The oral plaque dispersion agent according to any one of [1] to [3] above, wherein the component (A) has a chemical formula weight of preferably 120 or more, more preferably 130 or more, and 200 or less, preferably 180 or less, more preferably 160 or less.

[5] The oral plaque dispersion agent according to any one of [1] to [4] above, wherein the component (A) is preferably one or more selected from the group consisting of pentaerythritol, trimethylolmethane, trimethylolethane, trimethylolpropane, tris(hydroxymethyl)aminomethane, and triethanolamine, more preferably one or more selected from the group consisting of pentaerythritol, trimethylolethane, trimethylolpropane, tris(hydroxymethyl)aminomethane, and triethanolamine, still more preferably one or more selected from the group consisting of pentaerythritol, trimethylolethane, and trimethylolpropane, further more preferably pentaerythritol.

[6] The oral plaque dispersion agent according to any one of [1] to [5] above, wherein a content of the component (A) is preferably 0.2% by mass or more, more preferably 1% by mass or more, still more preferably 2% by mass or more, further preferably 4% by mass or more, and preferably 20% by mass or less, more preferably 18% by mass or less, still more preferably 15% by mass or less.

[7] The oral plaque dispersion agent according to any one of [1] to [6] above, further comprising (B) a sugar alcohol having 2 of primary hydroxyl groups in the chemical structure.

[8] The oral plaque dispersion agent according to any one of [1] to [7] above, wherein the component (B) is preferably one or more components (B1) selected from the group consisting of erythritol, xylitol, reduced palatinose, and mannitol, or is preferably one or two selected from the group consisting of sorbitol and glycerin; and the agent comprises, as component (B), preferably component (B1), more preferably one or two components selected from the group consisting of erythritol and xylitol, still more preferably erythritol.

[9] The oral plaque dispersion agent according to any one of [1] to [8] above, wherein a content of the component (B1) is preferably 1% by mass or more, more preferably 2% by mass or more, still more preferably 3% by mass or more, further preferably 5% by mass or more, and preferably 55% by mass or less, more preferably 50% by mass or less, still more preferably 40% by mass or less, further more preferably 30% by mass or less.

[10] The oral plaque dispersion agent according to any one of [1] to [9] above, wherein when the oral plaque dispersion agent of the present invention is a dentifrice, a content of the component (B1) is preferably 5% by mass or more, more preferably 10% by mass or more, still more preferably 15% by mass or more, and preferably 55% by mass or less, more preferably 50% by mass or less, still more preferably 45% by mass or less.

[11] The oral plaque dispersion agent according to any one of DJ to [9] above, wherein when the oral plaque dispersion agent of the present invention is a liquid, content of the component (B1) is preferably 1% by mass or more, more preferably 2% by mass or more, still more preferably 3% by mass or more, and preferably 20% by mass or less, more preferably 15% by mass or less, still more preferably 12% by mass or less.

[12] The oral plaque dispersion agent according to any one of [1] to [11] above, wherein a mass ratio of the component (A) to the component (B1), (A)/(B1), is preferably 0.01 or more, more preferably 0.05 or more, still more preferably 0.1 or more, further preferably 0.2 or more, and preferably 10 or less, more preferably 5 or less, still more preferably 3 or less, still more preferably 1 or less, still more preferably 0.8 or less.

[13] The oral plaque dispersion agent according to any one of [1] to [12] above, wherein in view of ensuring good flavor, in the oral plaque dispersion agent of the present invention, a content of component (B2) ranges preferably from 1 to 30% by mass, more preferably from 2 to 25% by mass, still more preferably from 3 to 20% by mass.

[14] The oral plaque dispersion agent according to any one of [1] to [13] above, further comprising (C) one or more protein-denaturing agents selected from the group consisting of urea, guanidine or a salt thereof, and an anionic surfactant.

[15] The oral plaque dispersion agent according to [14] above, wherein a content of the component (C) is preferably 0.001% by mass or more, more preferably 0.005% by mass or more, still more preferably 0.01% by mass or more, still more preferably 0.1% by mass or more, and preferably 1% by mass or less, more preferably 0.8% by mass or less, still more preferably 0.5% by mass or less.

[16] The oral plaque dispersion agent according to [14] or [15] above, wherein when the oral plaque dispersion agent of the present invention is a dentifrice, a content of the component (C) is preferably 0.1% by mass or more, more preferably 0.2% by mass or more, and preferably 2% by mass or less, more preferably 1.5% by mass or less, still more preferably 1.2% by mass or less.

[17] The oral plaque dispersion agent according to any one of [1] to [16] above, wherein a water content is preferably 50% by mass or more, more preferably 55% by mass or more, still more preferably 60% by mass or more, and preferably 99% by mass or less, more preferably 95% by mass or less, still more preferably 90% by mass or less, and when the oral plaque dispersion agent of the present invention comprises the component (B), component (C), or component (B) and component (C), the water content is preferably 90% by mass or less, more preferably 85% by mass or less.

[18] The oral plaque dispersion agent according to any one of [1] to [16] above, wherein when the oral plaque dispersion agent of the present invention is a dentifrice, a water content is preferably 12% by mass or more, more preferably 15% by mass or more, and preferably 55% by mass or less, more preferably 50a by mass or less, still more preferably 45% by mass or less.

[19] The oral plaque dispersion agent according to any one of [1] to [18] above, wherein a mass ratio of the component (A) to water, (A)/water, is preferably 0.01 or more, more preferably 0.02 or more, still more preferably 0.05 or more, and preferably 0.5 or less, more preferably 0.3 or less, still more preferably 0.2 or less.

[20] The oral plaque dispersion agent according to any one of [1] to [19] above, further comprising a cationic bactericide, wherein the cationic bactericide is preferably one or more selected from the group consisting of a quaternary ammonium compound and a biguanide compound, more preferably a quaternary ammonium compound, still more preferably one or two selected from the group consisting of cetylpyridinium chloride and benzethonium chloride.

[21] The oral plaque dispersion agent according to [20] above, wherein a content of the cationic bactericide is preferably 0.01% by mass or more, more preferably 0.02% by mass or more, still more preferably 0.03% by mass or more, and preferably 0.1% by mass or less, more preferably 0.08% by mass or less, still more preferably 0.07% by mass or less.

[22] The oral plaque dispersion agent according to any one of [1] to [21] above, wherein the dispersant is a dentifrice which is a toothpaste, a tooth powder or a gel dentifrice, or a liquid agent which is a mouthwash or a liquid dentifrice.

[23] Use of the oral plaque dispersion agent according to any one of [1] to [22] above, for dispersing dental plaque from the surface layer to the deep part of the dental plaque.

[24] Use of the oral plaque dispersion agent according to any one of [1] to [22] above, for removing dental plaque from the surface layer to the deep part of the dental plaque.

[25] A method for dispersing dental plaque from the surface layer to the deep part of the dental plaque, comprising applying the oral plaque dispersion agent according to any one of [1] to [22] above intraorally.

EXAMPLES

The present invention will be described in detail as follows on the basis of Examples. Note that unless otherwise specified in tables, the content of each component is indicated with % by mass.

Examples 1 to 10 and Comparative Examples 1 to 8

In accordance with formulations shown in tables 1 and 2, each oral plaque dispersion agent (all agents are liquid dispersion agent) was prepared. The thus obtained oral plaque dispersion agents were evaluated for dental plaque dispersibility according to the following method.

The results are shown in tables 1 and 2.

«Test on Effect of Ddispersing Dental Plaque»

1) Collection of Stimulating Saliva

Gum pellets included in Dentobuff Strip (OralCare Inc.) were chewed by healthy males in their twenties and thirties, and the saliva accumulated in the mouths was spit into falcon tubes every time thereby collecting saliva in the falcon tubes. Since there are individual differences in the bacteria in saliva, saliva collected from one healthy male was subjected to the test on the effect of dispersing dental plaque in all Examples and Comparative Examples.

2) Preparation of Dental Plaque Model

The saliva collected in each falcon tube was centrifuged at 3000 rpm/rt/10 min. The thus separated supernatant saliva was added with sucrose to prepare a 5% by mass solution, followed by stirring with a stirrer (voltex, NIPPON Genetics, Co., Ltd.), thereby preparing a dental plaque model test solution.

Next, one surface of each HAp substrate (Cosmo Bio Co., Ltd., 1 cm×1 cm) was mirror-polished using 40 μm-, 12 μm-m, and 3 μm-abrasive paper, and then the substrates were immersed in 1N HCl for 1 minute for acid decalcification treatment. After the treatment, the HAp substrates were washed with ion exchanged water, dried, and then placed in a 24-well plate. After 1 mL each of the above-prepared dental plaque model test solution was added, the resultant was stored together with a $CO_2$ pack in a plastic case to achieve anaerobic conditions, and then cultured at 37° C. for 48 hours.

3) Evaluation of Effect of Dispersing Dental Plaque

The saliva in the plate was sucked using a vacuum pump, and then 1 mL of ion exchanged water was added thereto, followed by shaking for 5 minutes. Next, water was sucked using a pump, 1 mL each of the dispersion agents obtained in tables 1 and 2 (paste dispersion agent was diluted with ion exchanged water to give a 4-fold diluted solution) was added to the respective wells, followed by shaking for 1 hour. The shaking was performed using a shaker (BioShake iQ (WakenBtech Co., Ltd)) under conditions of room temperature (25° C.) and 500 rpm.

Subsequently, each dispersion agent was sucked, and 1 mL of ion exchanged water was added, followed by shaking for 5 minutes. This procedure was repeated twice. Next, the water was sucked, and then 750 μL of a 0.1% by mass crystal violet (CV) solution was added thereto, followed by shaking for 15 minutes.

Furthermore, the CV-stained solution was sucked using a pump, and then 1 mL of ion exchanged water was added, followed by shaking for 5 minutes. This procedure was repeated twice. Next, the water was sucked using a pump, 500 mL of ethanol was added thereto, pipetting was performed, the extraction liquid was diluted 10-fold with ion exchanged water, and then absorbance at $OD_{595\ nm}$ was measured using a microplate recorder (TECAN, Wavelength variable absorbance microplate reader, SUNRISE RAINBOW THERMO).

Moreover, without using the above obtained dispersion agents, by using the absorbance at $OD_{595\ nm}$ (initial value) when merely washed with ion exchanged water as a reference value (100%), the dental plaque residual rates (%) were calculated according to the following formula.

Note that the lower the value of the dental plaque residual rate, the higher the effect of dispersing dental plaque.

Dental plaque residual rate={$OD_{595\ nm}$ when using a dispersion agent obtained above/$OD_{595\ nm}$ when merely washed with ion exchanged water}×100

TABLE 1

| Composition (% by mass) | Example 1 | Example 2 | Example 3 | Example 4 | Example 5 |
|---|---|---|---|---|---|
| (A) Pentaerythritol | 2 | 5 | 15 | 5 | 5 |
| Trimethylolpropane | 0 | 0 | 0 | 0 | 0 |
| Tris(hydroxymethyl)aminomethane | 0 | 0 | 0 | 0 | 0 |
| Triethanolamine | 0 | 0 | 0 | 0 | 0 |
| (B) Erythritol (B1) | 0 | 0 | 0 | 10 | 10 |
| Xylitol (B1) | 0 | 0 | 0 | 0 | 0 |
| Sorbitol (B2) | 0 | 0 | 0 | 0 | 0 |
| Glycerin (B2) | 0 | 0 | 0 | 0 | 0 |
| Sodium lauryl sulfate | 0 | 0 | 0 | 0 | 0.5 |
| Ion exchanged water | Balance | Balance | Balance | Balance | Balance |
| Total | 100 | 100 | 100 | 100 | 100 |
| Total water content | 98.0 | 95.0 | 85.0 | 85.0 | 84.5 |
| (A)/(B1) | — | — | — | 0.5 | 0.5 |
| (A)/Total water content | 0.02 | 0.05 | 0.18 | 0.06 | 0.06 |
| Dental plaque dispersibility (dental plaque residual rate, %) | 43 | 35 | 21 | 28 | 18 |

| Composition (% by mass) | Example 6 | Example 7 | Example 8 | Example 9 | Example 10 |
|---|---|---|---|---|---|
| (A) Pentaerythritol | 5 | 5 | 0 | 0 | 0 |
| Trimethylolpropane | 0 | 0 | 15 | 0 | 0 |
| Tris(hydroxymethyl)aminomethane | 0 | 0 | 0 | 15 | 0 |
| Triethanolamine | 0 | 0 | 0 | 0 | 15 |
| (B) Erythritol (B1) | 0 | 0 | 0 | 0 | 0 |
| Xylitol (B1) | 10 | 10 | 0 | 0 | 0 |
| Sorbitol (B2) | 0 | 0 | 0 | 0 | 0 |

TABLE 1-continued

| | | | | | |
|---|---|---|---|---|---|
| Glycerin (B2) | 0 | 0 | 0 | 0 | 0 |
| Sodium lauryl sulfate | 0 | 0.5 | 0 | 0 | 0 |
| Ion exchanged water | Balance | Balance | Balance | Balance | Balance |
| Total | 100 | 100 | 100 | 100 | 100 |
| Total water content | 85.0 | 84.5 | 85.0 | 85.0 | 85.0 |
| (A)/(B1) | 0.5 | 0.5 | — | — | — |
| (A)/Total water content | 0.06 | 0.06 | 0.18 | 0.18 | 0.18 |
| Dental plaque dispersibility (dental plaque residual rate, %) | 30 | 21 | 40 | 31 | 33 |

TABLE 2

| Composition (% by mass) | Comparative Example 1 | Comparative Example 2 | Comparative Example 3 | Comparative Example 4 |
|---|---|---|---|---|
| (A) Pentaerythritol | 0 | 0 | 0 | 0 |
| Trimethylolpropane | 0 | 0 | 0 | 0 |
| Tris(hydroxymethyl)aminomethane | 0 | 0 | 0 | 0 |
| Triethanolamine | 0 | 0 | 0 | 0 |
| (B) Erythritol (B1) | 15 | 15 | 0 | 0 |
| Xylitol (B1) | 0 | 0 | 15 | 15 |
| Sorbitol (B2) | 0 | 0 | 0 | 0 |
| Glycerin (B2) | 0 | 0 | 0 | 0 |
| Dipentaerythritol*[1] | 0 | 0 | 0 | 0 |
| Inositol*[2] | 0 | 0 | 0 | 0 |
| Sodium lauryl sulfate | 0 | 0.5 | 0 | 0.5 |
| Ion exchanged water | Balance | Balance | Balance | Balance |
| Total | 100 | 100 | 100 | 100 |
| Total water content | 85.0 | 84.5 | 85.0 | 84.5 |
| (A)/(B1) | 0.0 | 0.0 | 0.0 | 0.0 |
| (A)/Total water content | 0.00 | 0.00 | 0.00 | 0.00 |
| Dental plaque dispersibility (dental plaque residual rate, %) | 77 | 60 | 88 | 62 |

| Composition (% by mass) | Comparative Example 5 | Comparative Example 6 | Comparative Example 7 | Comparative Example 8 |
|---|---|---|---|---|
| (A) Pentaerythritol | 0 | 0 | 0 | 0 |
| Trimethylolpropane | 0 | 0 | 0 | 0 |
| Tris(hydroxymethyl)aminomethane | 0 | 0 | 0 | 0 |
| Triethanolamine | 0 | 0 | 0 | 0 |
| (B) Erythritol (B1) | 0 | 0 | 0 | 0 |
| Xylitol (B1) | 0 | 0 | 0 | 0 |
| Sorbitol (B2) | 15 | 0 | 0 | 0 |
| Glycerin (B2) | 0 | 15 | 0 | 0 |
| Dipentaerythritol*[1] | 0 | 0 | 1 | 0 |
| Inositol*[2] | 0 | 0 | 0 | 15 |
| Sodium lauryl sulfate | 0 | 0 | 0 | 0 |
| Ion exchanged water | Balance | Balance | Balance | Balance |
| Total | 100 | 100 | 100 | 100 |
| Total water content | 85.0 | 85.0 | 99.0 | 85.0 |
| (A)/(B1) | 0.0 | 0.0 | — | — |
| (A)/Total water content | 0.00 | 0.00 | 0.00 | 0.00 |
| Dental plaque dispersibility (dental plaque residual rate, %) | 102 | 95 | 100 | 90 |

*[1]chemical formula weight = 254, Number of primary hydroxyl groups in the molecular structure = 6
*[2]chemical formula weight = 180, Number of primary hydroxyl groups in the molecular structure = 0, Number of tertiary hydroxyl groups in the molecular structure = 6

Examples 11 to 15 and Comparative Examples 9 and 10

Table 3 shows the formulations of liquid dispersion agents. Table 4 shows the formulations of paste dispersion agents and liquid dispersion agents (paste dispersion agents in Examples 13 and 14 and Comparative Example 9, and liquid dispersion agents in Example 15 and Comparative Example 10).

TABLE 3

| Composition (% by mass) | | Example 11 | Example 12 |
|---|---|---|---|
| (A) | Pentaerythritol | 5 | 0 |
| | Trimethylolpropane | 0 | 15 |
| | Sodium lauryl sulfate | 0.5 | 0 |
| | Ion exchanged water | Balance | Balance |
| | Total | 100 | 100 |
| | Total water content | 94.5 | 85.0 |
| | (A)/Total water content | 0.05 | 0.18 |

TABLE 4

| Composition (% by mass) | Example 13 | Example 14 | Comparative Example 9 | Example 15 | Comparative Example 10 |
|---|---|---|---|---|---|
| (A) Pentaerythritol | 10.00 | 10.00 | 0.00 | 5.00 | 0.00 |
| (B) Erythritol (B1) | 25.00 | 25.00 | 35.00 | 2.00 | 7.00 |
| Sorbitol (B2) | 10.00 | 10.00 | 10.00 | 2.00 | 2.00 |
| Glycerin (B2) | 8.00 | 5.00 | 5.00 | 2.00 | 2.00 |
| Sodium lauryl sulfate | 1.00 | 1.00 | 1.00 | 0.00 | 0.00 |
| POE(40) hardened castor oil | 0.00 | 0.00 | 0.00 | 0.40 | 0.40 |
| Cetylpyridinium chloride | 0.02 | 0.02 | 0.02 | 0.05 | 0.05 |
| Propylene glycol | 0.00 | 0.00 | 0.00 | 0.50 | 0.50 |
| PEG600 | 2.00 | 2.00 | 2.00 | 0.13 | 0.13 |
| Sodium carboxymethyl cellulose | 0.60 | 0.60 | 0.60 | 0.00 | 0.00 |
| Xanthan gum | 0.10 | 0.10 | 0.10 | 0.00 | 0.00 |
| Abrasive silica | 0.00 | 3.00 | 3.00 | 0.00 | 0.00 |
| Saccharin sodium | 0.02 | 0.02 | 0.02 | 0.00 | 0.00 |
| Sucralose | 0.01 | 0.01 | 0.01 | 0.01 | 0.01 |
| Citric acid | 0.00 | 0.00 | 0.00 | 0.01 | 0.01 |
| Trisodium citrate | 0.00 | 0.00 | 0.00 | 0.05 | 0.05 |
| Flavor | 0.50 | 0.50 | 0.50 | 0.10 | 0.10 |
| Ion exchanged water | Balance | Balance | Balance | Balance | Balance |
| Total | 100 | 100 | 100 | 100 | 100 |
| Total water content | 42.8 | 42.8 | 42.8 | 87.8 | 87.8 |
| (A)/(B1) | 0.4 | 0.4 | 0.0 | 2.5 | 0.0 |
| (A)/Total water content | 0.23 | 0.23 | 0.00 | 0.06 | 0.00 |
| Form | Paste | Paste | Paste | Liquid | Liquid |

The invention claimed is:

1. A method for dispersing intraoral dental plaque, comprising applying intraorally an agent comprising
    (A) 4 to 15% by mass of a water-soluble compound having 3 or more primary hydroxyl groups in a molecular structure and 100 to 200 of a chemical formula weight as an active component in an oral cavity, wherein the component (A) is pentaerythritol
    (B) a sugar alcohol having 2 primary hydroxyl groups in the molecular structure wherein the component (B) is one or more components selected from the group consisting of erythritol, xylitol, reduced palatinose, and mannitol, and
    0.1 to 0.5% by mass of one or more protein-denaturing agents (C) selected from the group consisting of urea and sodium lauryl sulfate.

2. The method for dispersing intraoral dental plaque according to claim 1, further comprising one or more water-soluble component (D) having a number of primary hydroxy groups in a molecular structure of the component (D) from 4 to 6.

3. The method for dispersing intraoral dental plaque according to claim 2, wherein a solubility of the water-soluble component (D) to 100 g of water at 20° C. is 5 g/100 g or more.

4. The method for dispersing intraoral dental plaque according to claim 2, wherein the water-soluble component (D) has a chemical formula weight of 120 to 200.

5. The method for dispersing intraoral dental plaque according to claim 1, wherein the component (B) is one or more components selected from the group consisting of erythritol and xylitol.

6. The method for dispersing intraoral dental plaque according to claim 1, wherein a content of the component (B) is 1% by mass to 55% by mass.

7. The method for dispersing intraoral dental plaque according to claim 1, wherein a mass ratio of the component (A) to the component (B), (A)/(B), is 0.01 to 10.

8. The method for dispersing intraoral dental plaque according to claim 1, further comprising water, wherein a water content in the agent is 50% by mass to 99% by mass.

9. The method for dispersing intraoral dental plaque according to claim 1, wherein a mass ratio of the component (A) to water in the agent, (A)/water, is 0.01 to 0.5.

10. The method for dispersing intraoral dental plaque according to claim 1, wherein the agent further comprises a cationic bactericide.

11. The method for dispersing intraoral dental plaque according to claim 10, wherein the cationic bactericide is one or more selected from the group consisting of a quaternary ammonium compound and a biguanide compound.

12. The method for dispersing intraoral dental plaque according to claim 11, wherein a content of the cationic bactericide is 0.01% by mass to 0.1% by mass.

13. The method for dispersing intraoral dental plaque according to claim 1, wherein the agent is a toothpaste, a toothpowder, a gel dentifrice, a mouthwash, or a liquid dentifrice.

14. The method for dispersing intraoral dental plaque according to claim 1, which is a method for dispersing dental plaque from a surface layer to a deep part of the dental plaque.

15. The method for dispersing intraoral dental plaque according to claim 1, wherein said agent further comprises guanidine or a salt thereof.

* * * * *